United States Patent [19]

Clemens et al.

[11] 4,092,739
[45] June 6, 1978

[54] METHOD OF REPLACING HAIR

[76] Inventors: Richard P. Clemens, 1706 S. 91st Ave., Omaha, Nebr. 68124; Robert Fuchs, 1908 Parkwild West, Council Bluffs, Iowa 51501

[21] Appl. No.: 828,942

[22] Filed: Aug. 29, 1977

Related U.S. Application Data

[63] Continuation of Ser. No. 665,690, Mar. 10, 1976, abandoned.

[51] Int. Cl.² .......................... A61B 17/00; A61F 1/00
[52] U.S. Cl. ............................................. 3/1; 128/330
[58] Field of Search ................ 128/330, 334 R, 335.5; 3/1

[56] References Cited

U.S. PATENT DOCUMENTS

| | | | |
|---|---|---|---|
| 3,553,737 | 1/1971 | Bauman | 3/1 |
| 3,608,095 | 9/1971 | Barry | 3/1 |
| 3,625,220 | 12/1971 | Engelsher | 128/335 |
| 3,842,439 | 10/1974 | Connelly et al. | 3/1 |
| 3,858,245 | 1/1975 | Nate et al. | 3/1 |

Primary Examiner—Robert W. Michell
Assistant Examiner—Michael H. Thaler
Attorney, Agent, or Firm—George R. Nimmer

[57] ABSTRACT

A method of replacing hair to a delineated area of the human scalp to which, after surgically preparing the area, suturing is surgically embedded along an annular pathway. The suturing segmentally comprises a buried infra-length and neighboring supra-lengths surrounded by a tubular resinous sleeve which lies downwardly against the scalp skin layer. An apt connector means is attached to the resinous sleeves and to which connector the replacement hair might be attached.

3 Claims, 10 Drawing Figures

METHOD OF REPLACING HAIR

This is a continuation of application Ser. No. 665,690 filed Mar. 10, 1976 now abandoned.

This invention relates to a method of replacing hair to a delineated scalp area previously substantially devoid of natural hair. It is recognized that loss of hair resulting in complete or partial hair loss results in serious emotional problems, particularly among young males and females. An increasingly popular method for replacing hair is the so-called sutures-anchoring technique wherein sutures are surgically embeddably anchored into the human scalp, with suture lengths extending upwardly above the scalp skin and to which the cosmetic replacement hair is removably tied or otherwise mechanically associated. The sutures-anchoring technique is described in the prior U.S. Pat. Nos. 3,553,737 (Bauman-Jan. 12, 1971), 3,842,439 (Connelly-Oct. 22, 1974), and 3,914,801 (Dick-Oct. 28, 1975).

It is the general object of the present invention to provide a sutures-anchoring type method of replacing hair and which method has several advantages both surgically and structurally as compared to prior art techniques.

With such general objective in view, and other ancillary and related objectives which will become more apparent as this description proceeds, the method of replacing hair in a delineated area of a human scalp (which must be surgically prepared) generally comprises the following steps: embedding sutures along at least one annular pattern within the scalp delineated area, each suture being provided of surgical thread having alternating lengthwise segments including supra-length and infra-length segments, inserting the surgical thread through the scalp skin layer so that the infra-length will lie buried within the subcutaceous scalp layer and the two neighboring supra-lengths lie above and generally parallel to the scalp skin (and preferably an elongate one-piece surgical thread providing a plurality of buried infra-lengths); inserting the supra-lengths through tubular resinous sleeves that downwardly abut the scalp skin layer; applying removable buttress means to prevent the infra-length from sliding along the subcutaceous layer; and applying at least one apt connector means to the resinous sleeves and to which the cosmetic replacement hair might be attached.

In the drawing, wherein like characters refer to like parts in the several views, and in which.

Figure 1:
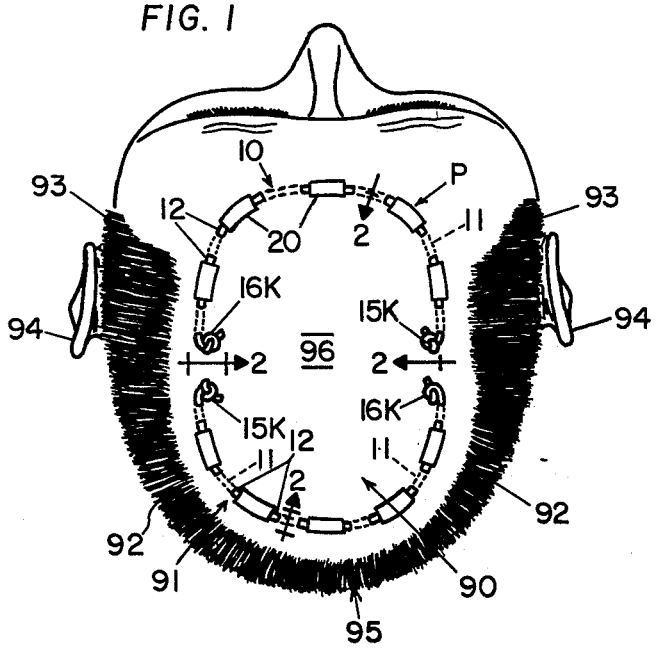
FIG. 1 is a top plan view of a human male scalp, showing suturing embedded in an annular pattern, each suture including a supra-length segment lying above and abuttably parallel with the scalp skin and securely surrounded by a tubular resinous sleeve.

Referring to FIG. 1, there is shown a human scalp 90 having a delineated area 91 substantially devoid of living hair. It will, of course, be recognized that the delineated area 91 may also have some hair on it. For purposes of illustration, the human person depicted in the accompanying drawing is of the male sex although this invention is equally applicable to the scalps of women. Surrounding the delineated area 91 is a fringe 92 of natural hair immediately adjacent the temples 93, the ears 94, and the nape of the neck 95. The scalp 90 in sectional elevation comprises three anatomical layers including the scalp skin 96, the subcutaceous layer 97, and the galea aponeurotical region 98.

Figure 10:
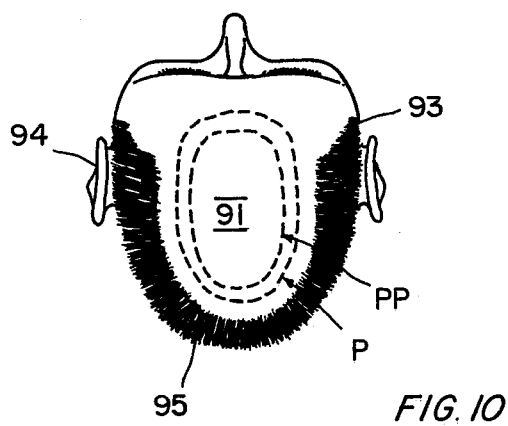
FIG. 10 is a schematic top plan view indicating that a plurality of sutured annular patterns might sometimes be employed.

A hair restoration operator initially delineates the area to be covered with replacement hair. The operator in making the delineation takes into account the contour of the existing hair and the personal preference of the person as to the final style the replacement hair should have. Although the delineated area 91, as shown in FIGS. 1 and 10, is oval it will, of course, be recognized that such an area can take on a variety of other shapes without deviating from the essence of the method of this invention.

The sevices of a medical doctor are required to surgically embed a series of sutures 10 in at least one annular pattern ("P", "PP", etc.) within the scalp delineated area 91. Prior to embedding the suturing 10, the delineated area 91 is surgically prepared and cleaned with an antiseptic following by numbing the area preferably using a local anesthetic. Aseptic conditions are maintained during the suture embedding procedure.

The suturing 10 is provided of a surgical thread having alternating lengths which will ultimately provide supra-length 12 and infra-length 11 segments. Each infra-length segment 11 lies buried within the subcutaceous layer 97, while the supra-length segments 12 (neighboring the respective buried infra-lengths 11) lie above and parallel to the scalp skin 96. As is well known in the surgical arts, the suturing thread leadward-length 15 is inserted downwardly through the scalp skin 96, thence along the subcutaceous layer 97, and thence upwardly through the scalp skin 96. Further, supra-lengths 12 are inserted through a longitudinally extending resinous sleeve 20 whereby the sleeves 20 are maintained snugly abuttably downwardly against the scalp skin 96. Moreover, to provide a desireable "shock-absorber" affect through the connector means (e.g. 30, 35, etc.), the resinous sleeves are of resiliently deformable resinous material (e.g. elastic) structural material such as polyurethane of the like. Typical dimensional parameters might include: three to six millimeters for the surgical thread diameter, about ¼ to 1 inch (and preferably about ¾ inch) for the infra-lengths 11, and about ¼ to one inch (and preferably about ¾ inch) for the tubular sleeves 20.

Figure 2:
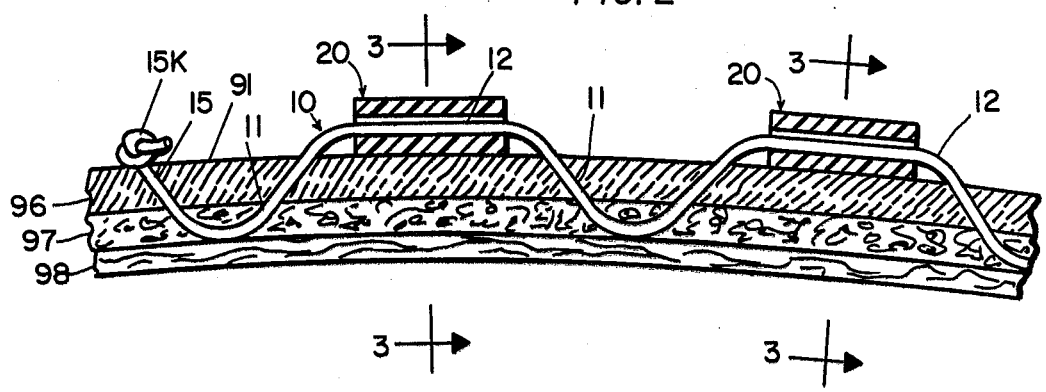
FIG. 2 is a longitudinally extending sectional elevational view taken along lines 2—2 of FIGS. 1 and 3.
Figure 3:
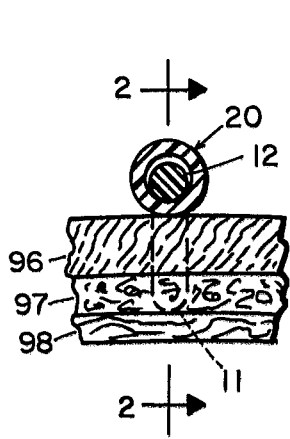
FIG. 3 is a transversely extending sectional elevational view taken along lines 3—3 of FIG. 2.

As is well recognized in the prior art, inert surgical thread materials are preferred so that upon healing of the scalp 96–97, the sutures are not rejected but rather the infra-lengths 11 lie buried within and compatible with the scalp layers 96–98. But in such condition, the embedded sutures 10 tend to be longitudinally slidable, and for this reason anti-sliding buttressing means are desireable. In FIGS. 1 and 2, the buttressing means comprises knotted ends 15K and 16K for the elongated surgical thread. However, the selected buttressing means (e.g. 15K, 16K, 40, etc.) is preferably removable so that there is permitted the freedom at some future date to replace the normally inherently slidable embedded sutures. For example, the two knots 15K and 16K can be clipped-off, thereby providing one type removable buttressing means. As is readily apparent from FIGS. 1 and 2, a single elongate length of surgical thread might be knotted at its leadward-length 15 and at its trail-length 16, whereby the intervening preponderant medial-length provides several interconnected infra-lengths 11 and alternating supra-lengths 12. In FIG. 1, two such elongated lengths of surgical thread respectively furnish a semi-circular array of sutures 10, both surgically embedded lengths together providing an oval annular pathway "P".

Figure 8:
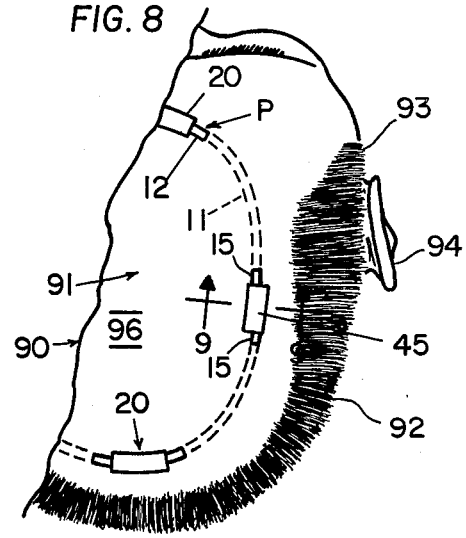
FIG. 8 is a detail top plan view of an alternate form removable buttress means.
Figure 9:
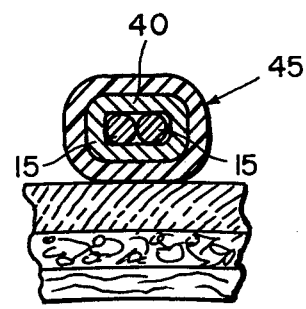
FIG. 9 is a transversely extending sectional elevational view taken along line 9—9 of FIG. 8.

FIGS. 8 and 9 suggest another form of removable buttressing means. Herein, the leadward-lengths 15 of the two arcuately embedded surgical threads are securely held together in a crimped metal-collar 40 which is surrounded by a resinous sheath 45. To remove this buttress means, the suturing leadward-ends 15 and trail-ends 16 are clipped-off nearby the crimped fasteners 40 whereby the entire continuous suturing is permitted to longitudinally slide out from the scalp layers. 96-97.

Replacement hair will need to be securely removably associated with the underlying anchoring means (e.g. sutures 10) as is well known in the prior art. Herein, the replacement hair is schematically indicated as an elongate string 80 to which is attached the cosmetic replacement hair (not shown). Whatever specific form the replacement hair takes, the forces applicable therefrom should be distributed fairly evenly among the several sleeves 20. In this vein, it is desireable to have regular spacing of infra-lengths 11 and sleeves 20 along the respective annular pathways ("P", "PP").

Figures 4, 5:
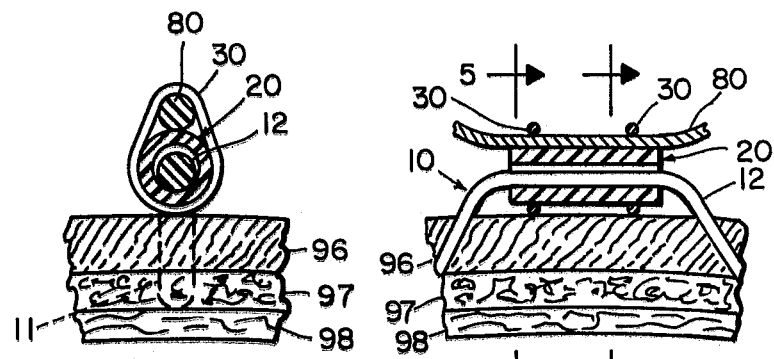
FIG. 4 is a longitudinally extending sectional elevational view like FIG. 2 wherein a pair of girth bands is applied as the connector means.
FIG. 5 is a transversely extending sectional elevational view taken along lines 5—5 of FIG. 4.
Figure 7:
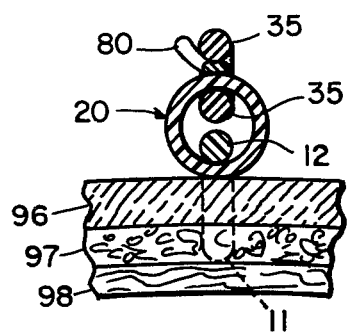
FIG. 7 is a transversely extending sectional elevational view taken along line 7—7 of FIG. 6.
Figure 6:
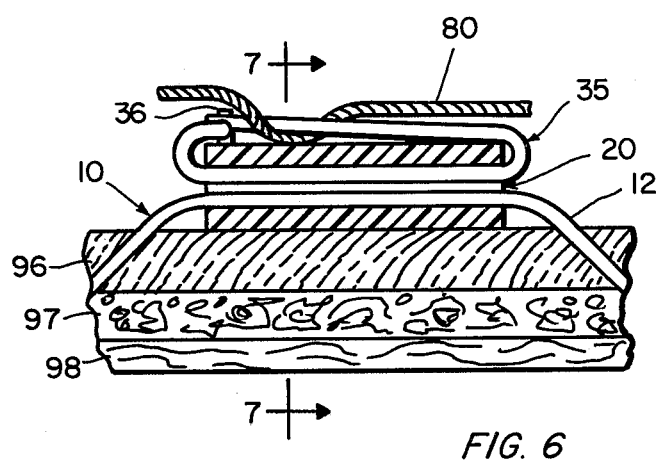
FIG. 6 is a longitudinally extending sectional elevational view like FIGS. 2 and 4 wherein a lengthy metallic clip is utilized as an alternate form connector means.

For securely removably associating the cosmetic replacement hair 80 to the suturing 10, there is an apt connector means intervening between the supra-lengths sleeves 20 and the replacement hair 80. The connector means should distribute the forces applicable from the replacement hair 80 longitudinally along each of the respective sleeves 20. In FIGS. 4 and 5, the intervening connector means comprises a plurality of girth-bands 30 surrounding each sleeve 20 and by which girth-bands 30 the string 80 is securely surrounded. Alternatively, the intervening connector means might extend longitudinally through the sleeve 20 alongside the supra-length 12. For example, as suggested in FIGS. 6 and 7, a longitudinal connector means might take the form of a springy metallic-clip 35 having a clasp 36 which performs analagously to a household safety-pin. The metallic-clip externally of resinous sleeve 20 surrounds the string 80.

As is suggested in the FIG. 10 schematic view, more than one annular pattern of sutures 10 might be advantageously employed. For example, annular patterns "P" and "PP" are shown as very closely spaced (about one-half inch apart) and at the periphery of delineated area 91, which in certain instances can faciliate the application and performance of the cosmetic replacement hair.

From the foregoing, the procedure and construction of the novel method for replacing hair will be readily understood and further explanation is believed to be unnecessary. However, since numerous modifications and changes will readily occur to those skilled in the art, it is not desired to limit the invention to the exact construction and procedures shown and described, and accordingly, all suitable modifications and equivalents may be resorted to, falling within the scope of the appended claims.

What is claimed is as follows:

1. A method for replacing hair in a delineated area of a living human scalp which has been surgically prepared, said method comprising the steps of:
   A. Positioning a plurality of individual tubular resinous sleeves atop the scalp skin layer and arranged in an annular pattern within said delineated area;
   B. Providing distinct spatial gaps between the ends of neighboring tubular sleeves;
   C. Embedding a series of sutures in an annular pattern utilizing an elongate one-piece surgical thread, the lead-end of which is inserted in repeated alternating fashion as follows:
      i. through the scalp skin layer and restricted to the spatial gap between neighboring sleeves whereby there is provided suturing infra-lengths lying buried within the subcutaceous scalp layer; and
      ii. through the longitudinal bore of the sleeves as a suturing supra-length said bore being sufficiently larger cross-sectionally than said suturing whereby each sleeve remains entirely atop the scalp skin layer and is slidable therealong;
   D. Buttressing the sutured elongate one-piece surgical thread at its lead-end and trail-end thereby preventing the buried infra-lengths thereof from sliding within the subcutaceous layer; and
   E. Applying at least one connector means to the sleeves and to which connector replacement hair might be attached.

2. The method of claim 1 comprising the step of inserting a portion of the connector longitudinally through the sleeve bore in parallelism to the suturing supra-length.

3. The method of claim 1 comprising the step of applying a plurality of girth bands around each sleeve as the connector means.

* * * * *